(12) United States Patent
Petermann et al.

(10) Patent No.: US 10,759,873 B2
(45) Date of Patent: *Sep. 1, 2020

(54) ESTERIFIED CELLULOSE ETHERS OF HIGH MOLECULAR WEIGHT AND HOMOGENEITY

(71) Applicant: Dow Global Technologies LLC, Midland, MI (US)

(72) Inventors: Oliver Petermann, Rellingen (DE); Matthias Sprehe, Walsrode (DE); Meinolf Brackhagen, Walsrode (DE)

(73) Assignee: Dow Global Technologies LLC, Midland, MI (US)

( * ) Notice: Subject to any disclaimer, the term of this patent is extended or adjusted under 35 U.S.C. 154(b) by 642 days.

This patent is subject to a terminal disclaimer.

(21) Appl. No.: 15/113,921

(22) PCT Filed: Jan. 27, 2015

(86) PCT No.: PCT/US2015/012981
§ 371 (c)(1),
(2) Date: Jul. 25, 2016

(87) PCT Pub. No.: WO2015/126576
PCT Pub. Date: Aug. 27, 2015

(65) Prior Publication Data
US 2016/0347866 A1    Dec. 1, 2016

Related U.S. Application Data

(60) Provisional application No. 61/942,371, filed on Feb. 20, 2014.

(51) Int. Cl.
| | | |
|---|---|---|
| C08B 13/00 | (2006.01) | |
| A61K 9/10 | (2006.01) | |
| A61K 47/38 | (2006.01) | |
| A61K 9/48 | (2006.01) | |
| C08B 11/20 | (2006.01) | |
| A61K 9/14 | (2006.01) | |
| A61K 9/28 | (2006.01) | |

(52) U.S. Cl.
CPC .......... C08B 13/00 (2013.01); A61K 9/10 (2013.01); A61K 9/4816 (2013.01); A61K 47/38 (2013.01); C08B 11/20 (2013.01); A61K 9/146 (2013.01); A61K 9/2866 (2013.01)

(58) Field of Classification Search
CPC ......... C08B 13/00; C08B 11/20; A61K 47/38; A61K 9/10; A61K 9/14; A61K 9/48; A61K 9/5047
See application file for complete search history.

(56) References Cited

U.S. PATENT DOCUMENTS

| | | | |
|---|---|---|---|
| 4,226,981 A | 10/1980 | Onda et al. | |
| 5,880,232 A | 3/1999 | Fujita et al. | |
| 2015/0202301 A1* | 7/2015 | Petermann | .............. C08B 11/20 |
| | | | 424/400 |
| 2015/0218198 A1* | 8/2015 | Petermann | .............. C08B 11/20 |
| | | | 424/463 |

FOREIGN PATENT DOCUMENTS

| | | |
|---|---|---|
| EP | 0219426 A2 | 4/1987 |
| JP | 1987-195395 | 8/1987 |
| JP | 2004-261132 | 9/2004 |
| JP | 2004262999 | 9/2004 |
| JP | 2007-262353 | 10/2007 |
| JP | 2010222428 | 10/2010 |
| WO | 2004089336 | 10/2004 |
| WO | 2005115330 A2 | 12/2005 |
| WO | 2006082518 A1 | 8/2006 |

(Continued)

OTHER PUBLICATIONS

Chen et al. Absolute molecular weight determination of hypromellose acetate succinate by size exclusion chromatography: Use of a multi angle laser light scattering detector and a mixed solvent. Journal of Pharmaceutical and Biomedical Analysis 56 (2011) 743-748.*

Viriden et al. Investigation of critical polymer properties for polymer release and swelling of HPMC matrix tablets. European Journal of Pharmaceutical sciences 36:297-309. (Year: 2009).*

Patel et al., Spray drying technology: an overview, Indian Journal of Science and Technology, vol. 2, No. 10, 2009, pp. 44-47.

Wu Souheng, Dynamic Rheology and Molecular Weight Distribution of Insoluble Polymers: Tetrafluorethylene-Hexafluoropropylene Copolymers, Central Research and Development Department, E.I. du Pont de Nemours and Company, Experimental Station, Delaware, American Chemical Society, 1985.

(Continued)

Primary Examiner — Lakshmi S Channavajjala

(57) ABSTRACT

Esterified cellulose ethers which have i) as ester groups aliphatic monovalent acyl groups or a combination of aliphatic monovalent acyl groups and groups of the formula —C(O)—R—COOA wherein R is a divalent aliphatic or aromatic hydrocarbon group and A is hydrogen or a cation, ii) a weight average molecular weight $M_w$ of from 80,000 Dalton to 220,000 Dalton, iii) a Polydispersity $M_w/M_n$ of from 1.3 to 4.0, and iv) an $M_z/M_n$ of not more than 18.5, when the weight average molecular weight $M_w$, the number average molecular weight Mn and the z-average molecular weight $M_z$ are measured by SEC-MALLS using as mobile phase a mixture produced from 40 parts by volume of acetonitrile and 60 parts by volume of aqueous buffer containing 50 mM $NaH_2$—$PO_4$ and 0.1 M $NaNO_3$. are useful as enteric polymers for pharmaceutical dosage forms.

17 Claims, No Drawings

(56) References Cited

FOREIGN PATENT DOCUMENTS

| WO | 2011159626 A1 | 12/2011 |
|---|---|---|
| WO | 2013148154 A1 | 10/2013 |
| WO | 2013154607 A1 | 10/2013 |
| WO | 2014031419 A1 | 2/2014 |
| WO | 2014031422 A1 | 2/2014 |
| WO | WO 2014031419 A1 * | 2/2014 |

OTHER PUBLICATIONS

Chen R., Characterization of Hypromellose Acetate Succinate by Size Exclusion Chromatography (SEC) Using Viscotek Triple Detector, International Journal of Polymer Anal. Charact., 2009, 14, pp. 617-630.

Chen R. et al., Absolute molecular weight determination of hypromellose acetate succinate by size exclusion chromatography: Use of a multi angle laser light scattering detector and a mixed solvent, Journal of Pharmaceutical and Biomedical Analysis, 2011, 56, pp. 743-748.

Wu S. et al., Aqueous Polymeric Coating for Pharmaceutic Dosage Forms, Drugs and the Pharmaceutical Sciences, 1997, pp. 385-418.

Podzimek, The Use of GPC Coupled with a Multiangle Laser Light Scattering Photometer for the Characterization of Polymers. On the Determination of Molecular Weight, Size, and Branching, Journal of Applied Polymer Science, 1994, vol. 54, pp. 91-103.

* cited by examiner

ESTERIFIED CELLULOSE ETHERS OF HIGH MOLECULAR WEIGHT AND HOMOGENEITY

FIELD

This invention concerns novel esterified cellulose ethers, solid dispersions of an active ingredient in such esterified cellulose ether, as well as liquid compositions, coated dosage forms and capsules comprising such esterified cellulose ether.

INTRODUCTION

Esters of cellulose ethers, their uses and processes for preparing them are generally known in the art. Various known esterified cellulose ethers are useful as enteric polymers for pharmaceutical dosage forms, such as hydroxypropyl methyl cellulose acetate succinate (HPMCAS). Enteric polymers are those that are resistant to dissolution in the acidic environment of the stomach. Dosage forms coated with such polymers protect the drug from inactivation or degradation in the acidic environment or prevent irritation of the stomach by the drug.

U.S. Pat. No. 4,365,060 discloses enterosoluble capsules which are said to have excellent enterosolubility behavior. The enterosoluble capsules are shaped with an ester of a cellulose ether that is esterified with acidic succinyl groups and aliphatic monovalent acyl groups. It is recommended that the cellulose ethers used for esterification have a molecular weight in the range from about 5000 to 200,000 to obtain adequate plasticity.

Wu et al. (Wu S. H. W., Wyatt D. M. and Adams M. W. 1997; *Chemistry and applications of cellulosic polymers for enteric coatings of solid dosage forms*; in McGinity J. W. (ed.), *Aqueous Coatings for Pharmaceutical Dosage Forms*, Marcel Dekker, New York, pp. 385-418) disclose molecular weights of commercially available different grades of HPMCAS. HPMCAS grade AS-L has an $M_w$ of 93,000, an $M_n$ of 46,000 (both measured by gel permeation chromatography method calibrated by polyethylene oxide) and an $M_w/M_n$ of 2.0; HPMCAS grade AS-M has an $M_w$ of 80,000, an $M_n$ of 44,000 and an $M_w/M_n$ of 1.8; and HPMCAS grade AS-H has an $M_w$ of 55,000 an $M_n$ of 33,000 and an $M_w/M_n$ of 1.7. HPMCAS grade AS-L, HPMCAS grade AS-M and HPMCAS grade AS-H which are currently commercially available from Shin-Etsu Chemical Co., Ltd. (Tokyo, Japan), known by the trade name "AQOAT", have higher average molecular weights $M_w$, but also a high polydispersity. A high polydispersity is an indication of some inhomogeneity in the molecular weight distribution of the esterified cellulose ether. When esterified cellulose ethers are used as enteric polymers for pharmaceutical dosage forms, inhomogeneity in the molecular weight distribution often leads to increased variability and reduced reproducibility of the properties of individual dosage forms, which decreases the predictability of the efficiency of the dosage forms. Furthermore, a high polydispersity is an indication of the presence of polymer chains which are much longer than the median polymer chains and which cause unduly long swelling and/or dissolution times and a sharp raise of viscosity with rising concentration when the esterified cellulose ethers are dissolved in a solvent. Moreover, the mentioned commercially available HPMCAS grade AS-L, HPMCAS grade AS-M and HPMCAS grade AS-H also have an increased turbidity in acetone solution. An increased turbidity in acetone solution is often undesirable, e.g., when the esterified cellulose ethers are used in transparent films or coatings.

U.S. Pat. No. 4,226,981 discloses a process for preparing mixed esters of cellulose ethers, such as hydroxypropyl methyl cellulose acetate succinate (HPMCAS), by esterifying hydroxypropyl methylcellulose with succinic anhydride and acetic anhydride in the presence of an alkali carboxylate as the esterification catalyst and acetic acid as the reaction medium. In the working examples 50 g of hydroxypropyl methyl cellulose is introduced into a reaction vessel equipped with a stirrer, 250 g of acetic acid, 50 g of sodium acetate, 15-60 g of succinic anhydride and 25-80 g of acetic anhydride are added and the reaction mixture is heated at 85° C. with agitation for 3 hours to effect esterification.

European Patent Application EP 0 219 426 discloses a process for producing an enteric-soluble acidic dicarboxylic acid ester of a cellulose ether wherein (a) a cellulose ether having hydroxypropoxyl groups as the ether-forming groups, of which a 2% by weight aqueous solution has a viscosity of at least 5 centipoise at 20° C., is reacted with (b) a dicarboxylic acid anhydride or a mixture thereof with an anhydride of an aliphatic monocarboxylic acid in the presence of (c) a combination of an alkali metal acetate and acetic acid.

A large number of presently known drugs have a low solubility in water, and thus complex techniques are required to prepare a dosage form. One known method includes dissolving such drug together with a pharmaceutically acceptable water-soluble polymer in an organic solvent that is optionally blended with water, and to spray-dry the solution. The pharmaceutically acceptable water-soluble polymer is aimed at reducing the crystallinity of the drug, thereby minimizing the activation energy necessary for the dissolution of the drug, as well as establishing hydrophilic conditions around the drug molecules, thereby improving the solubility of the drug itself to increase its bioavailability, i.e., its in vivo absorption by an individual upon ingestion.

International Patent Application WO 2005/115330 discloses hydroxypropyl methyl cellulose acetate (HPMCA) polymers and hydroxypropyl methyl cellulose acetate succinate (HPMCAS) polymers with a specific combination of substitution levels. The HPMCAS polymer has a degree of substitution of succinoyl groups ($DOS_S$) of at least 0.02, a degree of substitution of acetyl groups ($DOS_{Ac}$) of at least 0.65 and a sum of $DOS_{Ac}$ and $DOS_S$ of at least 0.85. The HPMCA polymer has a degree of substitution of acetyl groups ($DOS_{Ac}$) of at least 0.15. WO 2005/115330 discloses that the increased acetate substitution allows increased solubility of active agents in spray-dried solutions, while the increased succinate substitution increases the solubility of the polymer in aqueous solution.

International Patent Application WO 2011/159626 discloses an active ingredient and HPMCAS having a degree of substitution of methoxy groups ($DS_M$) of ≤1.45, and a combined degree of substitution of acetyl groups ($DS_{Ac}$) and succinoyl groups ($DS_S$) of ($DS_{Ac}+DS_S$)≥1.25.

However, in view of the large diversity of drugs, it is self-evident that a limited variety of esterified cellulose ethers having a high degree of substitution of acetyl groups and succinoyl groups cannot fulfill all needs.

Accordingly, it is one object of the present invention to provide new esterified cellulose ethers. It is a preferred object of the present invention to provide new esterified cellulose ethers which have a higher molecular weight than the HPMCAS grade AS-L, HPMCAS grade AS-M and HPMCAS grade AS-H described by Wu et al. as discussed further above but a lower polydispersity than the HPMCAS grade AS-L, HPMCAS grade AS-M and HPMCAS grade AS-H which are currently commercially available under the trade name "AQOAT". It is another preferred object of the present invention to provide new esterified cellulose ethers which have a lower turbidity in acetone solution than known hydroxyalkyl methyl cellulose acetate succinates at comparable $M_w$ and comparable degrees of substitution. Moreover, to facilitate processing of the esterified cellulose ethers and their incorporation into pharmaceutical dosage forms, such as in spray-drying procedures, it is another preferred object of the present invention to provide new esterified cellulose ethers which have a reasonably low viscosity in acetone.

SUMMARY

One aspect of the present invention is an esterified cellulose ether having i) as ester groups aliphatic monovalent acyl groups or a combination of aliphatic monovalent acyl groups and groups of the formula
—C(O)—R—COOA wherein R is a divalent aliphatic or aromatic hydrocarbon group and A is hydrogen or a cation,
i) as ester groups aliphatic monovalent acyl groups or a combination of aliphatic monovalent acyl groups and groups of the formula
—C(O)—R—COOA wherein R is a divalent aliphatic or aromatic hydrocarbon group and A is hydrogen or a cation,
ii) a weight average molecular weight $M_w$ of from 80,000 Dalton to 220,000 Dalton,
iii) a Polydispersity $M_w/M_n$ of from 1.3 to 4.0, and
iv) an $M_z/M_n$ of not more than 18.5,
when the weight average molecular weight $M_w$, the number average molecular weight $M_n$ and the z-average molecular weight $M_z$ are measured by SEC-MALLS using as mobile phase a mixture produced from 40 parts by volume of acetonitrile and 60 parts by volume of aqueous buffer containing 50 mM $NaH_2PO_4$ and 0.1 M $NaNO_3$.

Another aspect of the present invention is a composition comprising a liquid diluent and at least one esterified cellulose ether as described above.

Yet another aspect of the present invention is a solid dispersion comprising at least one active ingredient in at least one esterified cellulose ether as described above.

Yet another aspect of the present invention is a process for producing a solid dispersion which comprises the steps of blending a) at least one esterified cellulose ether as described above, b) one or more active ingredients and c) one or more optional additives, and subjecting the blend to extrusion.

Yet another aspect of the present invention is a process for producing a solid dispersion which comprises the steps of blending a) at least one esterified cellulose ether as described above, b) one or more active ingredients, c) one or more optional additives being different from components a) and b), and d) a liquid diluent to prepare a liquid composition, and removing said liquid diluent.

Yet another aspect of the present invention is a dosage form which is coated with the esterified cellulose ether as described above.

Yet another aspect of the present invention is a capsule shell which comprises the esterified cellulose ether as described above.

Yet another aspect of the present invention is a process for producing an esterified cellulose ether which comprises the steps of (A) dissolving or dispersing a cellulose ether and a first amount of alkali metal carboxylate in a reaction diluent, (B) heating the obtained mixture to a temperature of 60° C. to 110° C. before, during or after adding (i) an aliphatic monocarboxylic acid anhydride or (ii) a combination of an aliphatic monocarboxylic acid anhydride and a dicarboxylic acid anhydride to the mixture obtained in step (A), and allowing the esterification reaction to proceed, and (C) before the esterification reaction in step (B) is completed, adding a second amount of alkali metal carboxylate and allowing the esterification reaction to further proceed.

DETAILED DESCRIPTION

The esterified cellulose ether has a cellulose backbone having β-1,4 glycosidically bound D-glucopyranose repeating units, designated as anhydroglucose units in the context of this invention. The esterified cellulose ether preferably is an esterified alkyl cellulose, hydroxyalkyl cellulose or hydroxyalkyl alkylcellulose. This means that in the esterified cellulose ether of the present invention, at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ether. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses, ethylcelluloses, and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ether is an esterified hydroxyalkyl methylcellulose, such as hydroxypropyl methylcellulose.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylation agent, e.g. a methylation agent, and/or a hydroxyalkylation agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxy units are covalently bound to each other by ether bonding. Within this definition it is not important whether the terminal hydroxyl group of a hydroxyalkoxyl substituent is further alkylated, e.g. methylated, or not; both alkylated and non-alkylated hydroxyalkoxyl substituents are included for the determination of MS(hydroxyalkoxyl). The esterified cellulose ether of the invention generally has a molar substitution of hydroxyalkoxyl groups in the range 0.05 to 1.00, preferably 0.08 to 0.90, more preferably 0.12 to 0.70, most preferably 0.15 to 0.60, and particularly 0.20 to 0.50.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers according to this invention preferably have a DS(alkoxyl) in the range of 1.0 to 2.5, more preferably from 1.1 to 2.4, most preferably from 1.2 to 2.2 and particularly from 1.6 to 2.05.

Most preferably the esterified cellulose ether is an esterified hydroxypropyl methylcellulose having a DS(methoxyl) within the ranges indicated above for DS(alkoxyl) and an MS(hydroxypropoxyl) within the ranges indicated above for MS(hydroxyalkoxyl).

The esterified cellulose ether of the present invention has aliphatic monovalent acyl groups or a combination of aliphatic monovalent acyl groups and groups of the formula —C(O)—R—COOA, wherein R is a divalent aliphatic or aromatic hydrocarbon group and A is hydrogen or a cation. The cation preferably is an ammonium cation, such as $NH_4^+$ or an alkali metal ion, such as the sodium or potassium ion, more preferably the sodium ion. Most preferably, A is hydrogen.

The aliphatic monovalent acyl groups are preferably selected from the group consisting of acetyl, propionyl, and butyryl, such as n-butyryl or i-butyryl.

Preferred groups of the formula —C(O)—R—COOA are —C(O)—$CH_2$—$CH_2$—COOA, such as —C(O)—$CH_2$—$CH_2$—COOH or —C(O)—$CH_2$—$CH_2$—$COO^-Na^+$, —C(O)—CH═CH—COOA, such as —C(O)—CH═CH—COOH or —C(O)—CH═CH—$COO^-Na^+$, or —C(O)—$C_6H_4$—COOA, such as —C(O)—$C_6H_4$—COOH or —C(O)—$C_6H_4$—$COO^-Na^+$.

In the groups of formula —C(O)—$C_6H_4$—COOA the carbonyl group and the carboxylic group are preferably arranged in ortho-positions.

Preferred esterified cellulose ethers are
i) HPMCXY and HPMCX, wherein HPMC is hydroxypropyl methyl cellulose, X is A (acetate), or X is B (butyrate) or X is Pr (propionate) and Y is S (succinate), or Y is P (phthalate) or Y is M (maleate), such as hydroxypropyl methyl cellulose acetate phthalate (HPMCAP), hydroxypropyl methyl cellulose acetate maleate (HPMCAM), hydroxypropyl methylcellulose acetate succinate (HPMCAS), or hydroxypropyl methyl cellulose acetate (HPMCA); or
ii) hydroxypropyl cellulose acetate succinate (HPCAS), hydroxybutyl methyl cellulose propionate succinate (HBMCPrS), hydroxyethyl hydroxypropyl cellulose propionate succinate (HEHPCPrS); and methyl cellulose acetate succinate (MCAS).

Hydroxypropyl methylcellulose acetate succinate (HPMCAS) is the most preferred esterified cellulose ether.

The esterified cellulose ethers generally have a degree of substitution of aliphatic monovalent acyl groups, such as acetyl, propionyl, or butyryl groups, of 0.05 to 1.75, preferably of 0.10 to 1.50, more preferably of 0.15 to 1.25, and most preferably of 0.20 to 1.00. The esterified cellulose ethers generally have a degree of substitution of groups of formula —C(O)—R—COOA, such as succinoyl, of 0 to 1.6, preferably of 0.05 to 1.30, more preferably of 0.05 to 1.00, and most preferably of 0.10 to 0.70 or even 0.10 to 0.60.

The sum of i) the degree of substitution of aliphatic monovalent acyl groups and ii) the degree of substitution of groups of formula —C(O)—R—COOA is generally from 0.05 to 2.0, preferably from 0.10 to 1.4, more preferably from 0.20 to 1.15, most preferably from 0.30 to 1.55 and particularly from 0.40 to 1.00.

The content of the acetate and succinate ester groups is determined according to "Hypromellose Acetate Succinate, United States Pharmacopia and National Formulary, NF 29, pp. 1548-1550". Reported values are corrected for volatiles (determined as described in section "loss on drying" in the above HPMCAS monograph). The method may be used in analogue manner to determine the content of propionyl, butyryl, phthalyl and other ester groups.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left(\% \text{ MeO} * \frac{M(OCH_3) - M(OH)}{M(OCH_3)}\right) - \left(\% \text{ HPO} * \frac{M(OCH_2CH(OH)CH_3) - M(OH)}{M(OCH_2CH(OH)CH_3)}\right) - \left(\% \text{ Acetyl} * \frac{M(COCH_3) - M(H)}{M(COCH_3)}\right) - \left(\% \text{ Succinoyl} * \frac{M(COC_2H_4COOH) - M(H)}{M(COC_2H_4COOH)}\right)$$

$$DS(Me) = \frac{\frac{\% \text{ MeO}}{M(OCH_3)}}{\frac{\% \text{ cellulose backbone}}{M(AGU)}}$$

$$MS(HP) = \frac{\frac{\% \text{ HPO}}{M(HPO)}}{\frac{\% \text{ cellulose backbone}}{M(AGU)}}$$

$$DS(\text{Acetyl}) = \frac{\frac{\% \text{ Acetyl}}{M(\text{Acetyl})}}{\frac{\% \text{ cellulose backbone}}{M(AGU)}}$$

$$DS(\text{Succinoyl}) = \frac{\frac{\% \text{ Succinoyl}}{M(\text{Succinoyl})}}{\frac{\% \text{ cellulose backbone}}{M(AGU)}}$$

$$M(\text{MeO}) = M(OCH_3) = 31.03 \text{ Da}$$

$$M(HPO) = M(OCH_2CH(OH)CH_3) = 75.09 \text{ Da}$$

$$M(\text{Acetyl}) = M(COCH_3) = 43.04 \text{ Da}$$

$$M(\text{Succinoyl}) = M(COC_2H_4COOH) = 101.08 \text{ Da}$$

-continued $$M(AGU) = 162.14 \text{ Da}$$
$$M(OH) = 17.008 \text{ Da}$$
$$M(H) = 1.008 \text{ Da}$$

By convention, the weight percent is an average weight percentage based on the total weight of the cellulose repeat unit, including all substituents. The content of the methoxyl group is reported based on the mass of the methoxyl group (i.e., —OCH$_3$). The content of the hydroxyalkoxyl group is reported based on the mass of the hydroxyalkoxyl group (i.e., —O-alkylene-OH); such as hydroxypropoxyl (i.e., O—CH$_2$CH(CH$_3$)—OH). The content of the aliphatic monovalent acyl groups is reported based on the mass of —C(O)—R$_1$ wherein R$_1$ is a monovalent aliphatic group, such as acetyl (—C(O)—CH$_3$). The content of the group of formula —C(O)—R—COOH is reported based on the mass of this group, such as the mass of succinoyl groups (i.e., —C(O)—CH$_2$—CH$_2$—COOH).

The esterified cellulose ethers of the present invention have a weight average molecular weight M$_w$ of from 80,000 to 220,000 Dalton, preferably from 90,000 to 200,000 Dalton, more preferably from 90,000 to 185,000 Dalton, and most preferably from 100,000 to 180,000 Dalton.

The esterified cellulose ethers of the present invention have a Polydispersity M$_w$/M$_n$ of at least 1.3, typically at least 1.5 and more typically at least 1.8 or at least 2.0. Moreover, the esterified cellulose ethers of the present invention have a Polydispersity of up to 4.0, preferably of up to 3.5, more preferably up to 3.0, even more preferably up to 2.8, and most preferably of up to 2.6. The Polydispersity M$_w$/M$_n$ is calculated based on the determination of the weight average molecular weight M$_w$ and the number average molecular weight M$_n$.

The esterified cellulose ethers of the present invention have a ratio M$_z$/M$_n$ of not more than 18.5, preferably not more than 17.0, more preferably not more 15.5, and most preferably not more than 14.0 or 12.5 or 11.0. Typically the Mz/Mn ratio is 3.0 or more, more typically 5.0 or more, and most typically 7.0 or more.

The esterified cellulose ethers of the present invention generally have a number average molecular weight M$_n$ of from 30,000 to 100,000 Dalton, and preferably from 40,000 to 80,000 Dalton, or generally a z-average molecular weight, M$_z$, of from 450,000 to 1,500,000 Dalton or a combination thereof.

M$_w$, M$_n$ and M$_z$ are measured by SEC-MALLS using as mobile phase a mixture which has been produced by mixing 40 parts by volume of acetonitrile and 60 parts by volume of aqueous buffer containing 50 mM NaH$_2$PO$_4$ and 0.1 M NaNO$_3$. The mobile phase is adjusted to a pH of 8.0. SEC-MALLS stands for Size Exclusion Chromatography coupled with a mass sensitive Multi Angle Laser Light Scattering detector. The procedure is described in Journal of Pharmaceutical and Biomedical Analysis 56 (2011) 743-748. The measurement of M$_w$, M$_n$ and M$_z$ is described in more details in the Examples.

The esterified cellulose ethers of the present invention preferably have a viscosity of up to 4.0 mPa·s, more preferably up to 3.6 mPa·s, and most preferably up to 3.2 mPa·s, measured as a 2.0 wt % solution of the esterified cellulose ether in 0.43 wt % aqueous NaOH at 20° C. Generally the viscosity is at least 2.4 mPa·s, typically at least 2.5 mPa·s, measured as a 2.0 wt % solution of the esterified cellulose ether in 0.43 wt % aqueous NaOH at 20° C. The 2.0% by weight solution of the esterified cellulose ether is prepared as described in"Hypromellose Acetate Succinate, United States Pharmacopia and National Formulary, NF 29, pp. 1548-1550", followed by an Ubbelohde viscosity measurement according to DIN 51562-1:1999-01 (January 1999).

The esterified cellulose ethers of the present invention have a higher weight average molecular weight M$_w$ than could be expected based on its viscosity, measured as a 2.0 wt % solution of the esterified cellulose ether in 0.43 wt % aqueous NaOH at 20° C. Without wanting to be bound by the theory, it is believed that this higher molecular weight is created by hydrophobic/hydrophilic chain association and/or crosslinking reactions.

The combination of high weight average molecular weight M$_w$, reasonably low M$_w$/M$_n$ and low M$_z$/M$_n$ makes the esterified cellulose ether of the present invention very suitable as enteric polymer for pharmaceutical dosage forms. The high molecular weight of the esterified cellulose ether provides heightened resistance against gastric juice. The reasonably low M$_w$/M$_n$ of the esterified cellulose ether of the present invention is an indication of the fairly homogeneous molecular weight distribution of the esterified cellulose ether. Reasonably high homogeneity is desirable for enteric polymers for pharmaceutical dosage forms to increase reproducibility of the properties of individual dosage forms, which maximizes the predictability of the efficiency of the dosage forms.

Moreover, esterified cellulose ethers of a low viscosity of up to 4.0 mPa·s, measured as a 2.0 wt % solution of the esterified cellulose ether in 0.43 wt % aqueous NaOH at 20° C., can be efficiently produced. It has been found that the viscosity of the esterified cellulose ether in 0.43 wt % aqueous NaOH substantially corresponds to the viscosity of the cellulose ether which is useful as a starting material for producing the esterified cellulose ether. A low viscosity cellulose ether used as a starting material allows a good miscibility of the reaction mixture used for producing the esterified cellulose ethers of the present invention resulting in a homogeneous reaction mixture.

It has been found that the esterified cellulose ethers of the present invention exhibit a lower turbidity as 1.5 weight percent solution in acetone than known esterified cellulose ethers of comparable weight average molecular weight M$_w$ and comparable degrees of substitution, which satisfies a long-felt need. Without wanting to be bound to the theory, it is believed that the low M$_z$/M$_n$ makes a significant contribution to the surprisingly low turbidity. The turbidity is typically 10 NTU or more, more typically 12 NTU or more, and typically up to 19 NTU, more typically only up to 18 NTU, and under optimized production conditions even only up to 16 NTU, measured as 1.5 weight percent solution in acetone. The NTU measurement in acetone is described in details in the Examples section. Esterified cellulose ethers exhibiting a low turbidity are excellent film-forming polymers or other components of transparent coatings, of other films or capsules. Moreover, the esterified cellulose ethers of the present invention often exhibit a lower viscosity in acetone than known esterified cellulose ethers of comparable weight average molecular weight M$_w$. Typically the esterified cellulose ethers of the present invention have a viscosity of up to 21 mPa·s, measured as a 10 wt % solution of the esterified cellulose ether in acetone at 20° C. This facilitates spraying of organic solution of the esterified cellulose ethers onto dosage forms, such as tablets, to be coated.

Another aspect of the present invention is a process for producing an esterified cellulose ether which comprises the steps of (A) dissolving or dispersing a cellulose ether and a first amount of alkali metal carboxylate in a reaction diluent, (B) heating the obtained mixture to a temperature of 60° C. to 110° C. before, during or after adding (i) an aliphatic monocarboxylic acid anhydride or (ii) a combination of an aliphatic monocarboxylic acid anhydride and a dicarboxylic acid anhydride to the mixture obtained in step (A), and allowing the esterification reaction to proceed, and (C) before the esterification reaction in step (B) is completed, adding a second amount of alkali metal carboxylate and allowing the esterification reaction to further proceed. At least according to preferred embodiments of this process the novel esterified cellulose ethers of the present invention are achieved.

In step (A) the cellulose ether and a first amount of alkali metal carboxylate, such as sodium acetate or potassium acetate, are dissolved or dispersed in a reaction diluent. First the cellulose ether or first the alkali metal carboxylate or both simultaneously can be dissolved or dispersed in the reaction diluent. Only a portion of the total amount of alkali metal carboxylate that is added to the reaction mixture in the esterification process of present invention is added to the cellulose ether in step (A). Preferably only 15 to 35 percent, more preferably only 20 to 30 percent of the total added amount of alkali metal carboxylate is added in step (A). Preferably a cellulose ether is used which has the type of ether groups and the degree(s) of substitution of ether groups as described further above. The cellulose ether generally has a viscosity of from 1.2 to 5 mPa·s, preferably from 2.4 to 5 mPa·s, more preferably from 2.5 to 4 mPa·s, and most preferably from 2.5 to 3.8 mPa·s, measured as a 2 weight-% aqueous solution at 20° C. according to ASTM D2363-79 (Reapproved 2006). Cellulose ethers of such viscosity can be obtained by subjecting a cellulose ether of higher viscosity to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent.

A preferred reaction diluent is an aliphatic carboxylic acid, such as acetic acid, propionic acid, or butyric acid. The reaction diluent can comprise minor amounts of other solvents or diluents which are liquid at room temperature and do not react with the cellulose ether, such as aromatic or aliphatic solvents like benzene, toluene, 1,4-dioxane, or tetrahydrofurane; or halogenated $C_1$-$C_3$ derivatives, like dichloro methane or dichloro methyl ether, but the amount of the aliphatic carboxylic acid is preferably more than 50 percent, more preferably at least 75 percent, and even more preferably at least 90 percent, based on the total weight of the reaction diluent. Most preferably the reaction diluent consists of an aliphatic carboxylic acid. The molar ratio [aliphatic carboxylic acid/anhydroglucose units of cellulose ether] generally is from [4.9/1.0] to [11.5/1.0], preferably from [5.5/1.0] to [11.0/1.0], more preferably from [5.7/1.0] to [10.0/1.0].

In step (B) the obtained mixture is heated to a temperature of 60° C. to 110° C., preferably 70 to 100° C., before, during or after adding (i) an aliphatic monocarboxylic acid anhydride or (ii) a combination of an aliphatic monocarboxylic acid anhydride and a dicarboxylic acid anhydride to the reaction mixture which has been obtained in step (A) and which comprises the cellulose ether, the reaction diluent and the above-mentioned first amount of the alkali metal carboxylate. Preferred aliphatic monocarboxylic acid anhydrides are selected from the group consisting of acetic anhydride, butyric anhydride and propionic anhydride. Preferred dicarboxylic acid anhydrides are selected from the group consisting of succinic anhydride, maleic anhydride and phthalic anhydride. If an aliphatic monocarboxylic acid anhydride and a dicarboxylic acid anhydride are used in combination, the two anhydrides may be introduced into the reaction vessel at the same time or separately one after the other. The amount of each anhydride to be introduced into the reaction vessel is determined depending on the desired degree of esterification to be obtained in the final product, usually being 1 to 10 times the stoichiometric amounts of the desired molar degree of substitution of the anhydroglucose units by esterification. The molar ratio between the anhydride of an aliphatic monocarboxylic acid and the anhydroglucose units of the cellulose ether generally is 0.9 or more, and preferably 1 or more. The molar ratio between the anhydride of an aliphatic monocarboxylic acid and the anhydroglucose units of the cellulose ether generally is 8 or less, preferably 6 or less, and more preferably 4 or less. If an anhydride of a dicarboxylic acid is used, the molar ratio between the anhydride of a dicarboxylic acid and the anhydroglucose units of cellulose ether generally is 0.1 or more, and preferably 0.13 or more. The molar ratio between the anhydride of a dicarboxylic acid and the anhydroglucose units of cellulose ether generally is 1.5 or less, and preferably 1 or less. The molar number of anhydroglucose units of the cellulose ether utilized in the process of the present invention can be determined from the weight of the cellulose ether used as a starting material, by calculating the average molecular weight of the substituted anhydroglucose units from the DS(alkoxyl) and MS(hydroxyalkoxyl). In step (B) the esterification reaction is allowed to proceed for a period of time that is sufficient to partially complete the reaction, typically up to 60 minutes, more typically from 15 to 45 min.

Before the esterification reaction in step (B) is completed, in step (C) a second amount of alkali metal carboxylate is added to the reaction mixture and the esterification reaction is allowed to further proceed. Preferably 65 to 85 percent, more preferably 70 to 80 percent of the total added amount of alkali metal carboxylate is added in step (C). The reaction mixture is then kept at 60° C. to 110° C., preferably at 70 to 100° C., for an additional period of time sufficient to complete the reaction, that is, typically from 2 to 8 hours, more typically from 2 to 5 hours.

The total amount of alkali metal carboxylate added in steps (A) and (C) is preferably such that molar ratio [alkali metal carboxylate/anhydroglucose units of cellulose ether] is from [1.0/1.0] to [3.5/1.0], more preferably from [1.1/1.0] to [3.0/1.0], and most preferably from [1.9/1.0] to [2.5/1.0].

After completion of the esterification reaction, the reaction product can be precipitated from the reaction product mixture in a known manner, for example by contacting the reaction product mixture with a large volume of water, such as described in U.S. Pat. No. 4,226,981, International Patent Application WO 2005/115330 or European Patent Application EP 0 219 426. In a preferred embodiment of the invention the reaction product is precipitated from the reaction mixture as described in International Patent Application PCT/US13/030394, published as WO2013/148154, to produce an esterified cellulose ether in the form of a powder.

Another aspect of the present invention is a composition comprising a liquid diluent and one or more of the above described esterified cellulose ethers. The term "liquid diluent" as used herein means a diluent that is liquid at 25° C. and atmospheric pressure. The diluent can be water or an organic liquid diluent or a mixture of water and an organic liquid diluent. Preferably the amount of the liquid diluent is sufficient to provide sufficient fluidity and processability to the composition for the desired usage, such as spray-drying.

The term "organic liquid diluent" as used herein means an organic solvent or a mixture of two or more organic solvents. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; or nitriles, such as acetonitrile. More preferably the organic liquid diluents have 1 to 6, most preferably 1 to 4 carbon atoms, such as methanol, ethanol, isopropylalcohol, or n-propanol. In one embodiment the composition of the present invention comprises as liquid diluent an organic diluent alone or mixed with a minor amount of water. In this embodiment the composition of the present invention preferably comprises more than 50, more preferably at least 65, and most preferably at least 75 weight percent of an organic liquid diluent and preferably less than 50, more preferably up to 35, and most preferably up to 25 weight percent of water, based on the total weight of the organic liquid diluent and water. This embodiment of the invention is of particularly useful if the present invention comprises an active ingredient of poor water solubility.

In another embodiment the composition of the present invention comprises as liquid diluent water alone or mixed with a minor amount of an organic liquid diluent as described above. In this embodiment the composition of the present invention preferably comprises at least 50, more preferably at least 65, and most preferably at least 75 weight percent of water and preferably up to 50, more preferably up to 35, and most preferably up to 25 weight percent of an organic liquid diluent, based on the total weight of the organic liquid diluent and water. This embodiment of the invention is particularly useful for providing coatings or capsules from aqueous compositions comprising the esterified cellulose ether of the present invention. When preparing an aqueous solution, it is preferred that at least a portion of the groups of formula —C(O)—R—COOA are in their salt form.

The composition of the present invention comprising a liquid diluent and one or more of the above described esterified cellulose ethers is useful as an excipient system for active ingredients and particularly useful as an intermediate for preparing an excipient system for active ingredients, such as fertilizers, herbicides or pesticides, or biologically active ingredients, such as vitamins, herbals and mineral supplements and drugs. Accordingly, the composition of the present invention preferably comprises one or more active ingredients, most preferably one or more drugs. The term "drug" is conventional, denoting a compound having beneficial prophylactic and/or therapeutic properties when administered to an animal, especially humans. Preferably, the drug is a "low-solubility drug", meaning that the drug has an aqueous solubility at physiologically relevant pH (e.g., pH 1-8) of about 0.5 mg/mL or less. The invention finds greater utility as the aqueous solubility of the drug decreases. Thus, compositions of the present invention are preferred for low-solubility drugs having an aqueous solubility of less than 0.1 mg/mL or less than 0.05 mg/mL or less than 0.02 mg/mL, or even less than 0.01 mg/mL where the aqueous solubility (mg/mL) is the minimum value observed in any physiologically relevant aqueous solution (e.g., those with pH values between 1 and 8) including USP simulated gastric and intestinal buffers. The active ingredient does not need to be a low-solubility active ingredient in order to benefit from this invention, although low-solubility active ingredients represent a preferred class for use with the invention. An active ingredient that exhibits appreciable aqueous solubility in the desired environment of use may have an aqueous solubility up to 1 to 2 mg/mL, or even as high as 20 to 40 mg/mL. Useful low-solubility drugs are listed in the International Patent Application WO 2005/115330, pages 17-22.

The composition of the present invention preferably comprises from 1 to 40 weight percent, more preferably from 2.5 to 30 weight percent, most preferably from 5 to 25 weight percent, and particularly from 7 to 20 percent of at least one esterified cellulose ether as described above, from 40 to 99 weight percent, more preferably from 54.9 to 97.4 weight percent, most preferably from 65 to 94.5 weight percent and particularly from 70 to 92 percent of a liquid diluent described further above, and from 0 to 40 percent, preferably from 0.1 to 40 percent, most preferably from 0.5 to 25 percent, and particularly from 1 to 15 percent of an active ingredient, based on the total weight of the composition.

In one aspect of the invention the composition comprising at least one esterified cellulose ether as described above, one or more active ingredients and optionally one or more adjuvants can be used in liquid form, for example in the form of a suspension, a slurry, a sprayable composition, or a syrup. The liquid composition is useful, e.g., for oral, ocular, topical, rectal or nasal applications. The liquid diluent should generally be pharmaceutically acceptable, such as ethanol or glycerol, optionally mixed with water as described above.

In another aspect of the invention the liquid composition of the present invention is used for producing a solid dispersion comprising at least one active ingredient, such as a drug described further above, at least one esterified cellulose ether as described above and optionally one or more adjuvants. The solid dispersion is produced by removing the liquid diluent from the composition.

One method of removing the liquid diluent from the liquid composition is by casting the liquid composition into a film or a capsule or by applying the liquid composition onto a solid carrier that in turn may comprise an active ingredient. A preferred method of producing the solid dispersion is by spray-drying. The term "spray-drying" refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). A useful spray-drying process is described in the International Patent Application WO 2005/115330, page 34, line 7 page—35, line 25.

Alternatively, the solid dispersion of the present invention may be prepared by i) blending a) at least one esterified cellulose ether defined above, b) one or more active ingredients and c) one or more optional additives being different from components a) and b), and ii) subjecting the blend to extrusion. The term "extrusion" as used herein includes processes known as injection molding, melt casting and compression molding. Techniques for extruding, preferably for melt-extruding compositions comprising an active ingredient such as a drug are known and described by Joerg Breitenbach, Melt extrusion: from process to drug delivery technology, *European Journal of Pharmaceutics and Biopharmaceutics* 54 (2002) 107-117 or in European Patent Application EP 0 872 233. The above-mentioned components a), b) and optionally c) are preferably mixed in the form of particles, more preferably in powdered form. The components a), b) and optionally c) may be pre-mixed before feeding the blend into a device utilized for extrusion. Useful devices for extrusion, specifically useful extruders, are known in the art. Alternatively, the components a), b) and optionally c) may be fed separately into the extruder and blended in the device before or during a heating step. After extrusion the extrudate may be easily shaped, molded, chopped, spheronized into beads, cut into strands, tabletted or otherwise processed to the desired physical form. The extrudate can optionally be cooled to hardening and ground into a powdered form.

The solid dispersion of the present invention preferably comprises from 20 to 99.9 percent, more preferably from 30 to 98 percent, and most preferably from 60 to 95 percent of an esterified cellulose ether a) as described above, and preferably from 0.1 to 80 percent, more preferably from 2 to 70 percent, and most preferably from 5 to 40 percent of an active ingredient b), based on the total weight of the esterified cellulose ether a) and the active ingredient b). The combined amount of the esterified cellulose ether a) and the active ingredient b) is preferably at least 70 percent, more preferably at least 80 percent, and most preferably at least 90 percent, based on the total weight of the solid dispersion. The remaining amount, if any, are one or more of the adjuvants c) which are different from components a) and b) and which are described in more detail below. The solid dispersion can comprise one or more of the esterified cellulose ethers a), one or more of the active ingredients b), and optionally one or more of the adjuvants c), however their total amount is generally within the above-mentioned ranges.

Once the solid dispersion comprising at least one active ingredient in at least one esterified cellulose ether has been formed, several processing operations can be used to facilitate incorporation of the dispersion into a dosage form. These processing operations include drying, granulation, and milling. The inclusion of optional adjuvants in the solid dispersion may be useful in order to formulate the composition into dosage forms. The solid dispersion of the present invention may be in various forms, such as, e.g. in the form of strands, pellets, granules, pills, tablets, caplets, microparticles, fillings of capsules or injection molded capsules or in the form of a powder, film, paste, cream, suspension or slurry.

The amount of the active ingredient in the dosage form is generally is at least 0.1 percent, preferably at least 1 percent, more preferably at least 3 percent, most preferably at least 5 percent and generally up to 70 percent, preferably up to 50 percent, more preferably up to 30 percent, most preferably up to 25 percent, based on the total weight of the dosage form.

In another aspect of the invention the composition of the present invention comprising a liquid diluent and one or more of the above described esterified cellulose ethers may be used for coating dosage forms, such as tablets, granules, pellets, caplets, lozenges, suppositories, pessaries or implantable dosage forms, to form a coated composition. If the composition of the present invention comprises an active ingredient, such as a drug, drug layering can be achieved, i.e., the dosage form and the coating may comprise different active ingredients for different end-uses and/or having different release kinetics.

In yet another aspect of the invention the composition of the present invention comprising a liquid diluent and one or more of the above described esterified cellulose ethers may be used for the manufacture of capsules in a process which comprises the step of contacting the liquid composition with dipping pins.

The liquid composition and the solid dispersion of the present invention may further comprise optional additives, such as coloring agents, pigments, opacifiers, flavor and taste improvers, antioxidants, and any combination thereof. Optional additives are preferably pharmaceutically acceptable. Useful amounts and types of one or more optional adjuvants are generally known in the art and depend on the intended end-use of the liquid composition or the solid dispersion of the present invention.

The following examples are for illustrative purposes only and are not intended to limit the scope of the present invention.

EXAMPLES

Unless otherwise mentioned, all parts and percentages are by weight. In the Examples the following test procedures are used.

Content of Ether and Ester Groups

The content of ether groups in the esterified cellulose ether is determined in the same manner as described for "Hypromellose", United States Pharmacopeia and National Formulary, USP 35, pp 3467-3469.

The ester substitution with acetyl groups (—CO—CH$_3$) and the ester substitution with succinoyl groups (—CO—CH$_2$—CH$_2$—COOH) are determined according to Hypromellose Acetate Succinate, United States Pharmacopia and National Formulary, NF 29, pp. 1548-1550". Reported values for ester substitution are corrected for volatiles (determined as described in section "loss on drying" in the above HPMCAS monograph).

Viscosity of Hydroxypropyl Methyl Cellulose (HPMC) Samples

The viscosity of the HPMC samples was measured as a 2.0% by weight solution in water at 20° C.±0.1° C. The 2.0% by weight HPMC solution in water was prepared according to United States Pharmacopeia (USP 35, "Hypromellose", pages 3467-3469), followed by an Ubbelohde viscosity measurement according to DIN 51562-1:1999-01 (January 1999).

Viscosity of Hydroxypropyl Methyl Cellulose Acetate Succinate (HPMCAS)

The 2.0% by weight solution of the HPMCAS in 0.43 wt % aqueous NaOH was prepared as described in"Hypromellose Acetate Succinate, United States Pharmacopia and National Formulary, NF 29, pp. 1548-1550", followed by an Ubbelohde viscosity measurement at 20° C. according to DIN 51562-1:1999-01 (January 1999).

The 10 wt % solution of HPMCAS in acetone was prepared by first determining the loss on drying of the HPMCAS according "Hypromellose Acetate Succinate, United States Pharmacopia and National Formulary, NF 29, pp. 1548-1550". Subsequently 10.00 g HPMCAS, based on its dry weight, was mixed with 100 g of acetone under vigorous stirring at room temperature. The mixture was rolled on a roller mixer for about 24 hours. The solution was centrifuged at 2000 rpm for 3 minutes using a Megafuge 1.0 centrifuge, commercially available from Heraeus Holding GmbH, Germany, followed by an Ubbelohde viscosity measurement at 20° C. according to DIN 51562-1:1999-01 (January 1999).

Determination of the Turbidity

An 1.5 weight % solution of HPMCAS in acetone was prepared by mixing the HPMCAS with acetone and stirring the mixture at room temperature for 24 hours. The turbidity was analyzed with the Turbidimeter 2100AN (wolfram lamp, German catalogue number 47089-00) (Hach Company, Loveland, Colo., USA). The turbidity was the analysis of the scattered light through a sample cell (diameter: 24 mm) and is given in NTUs (nephelometric turbidity units) according to USEPA method 180.1. The analysis was performed against a formazin standard ranging from <0.1 NTU to 7500 NTU (StablCal™, catalogue number 2659505). A USEPA method 180.1 filter module (catalogue number 3031200) was used.

Determination of $M_w$, $M_n$ and $M_z$

Mw, Mn and Mz are measured according to Journal of Pharmaceutical and Biomedical Analysis 56 (2011) 743-747 unless stated otherwise. The mobile phase was prepared by mixing mixture of 40 parts by volume of acetonitrile and 60 parts by volume of aqueous buffer containing 50 mM NaH2PO4 and 0.1 M NaNO3. The mobile phase was adjusted to a pH of 8.0. Solutions of the cellulose ether esters were filtered into a HPLC vial through a syringe filter of 0.45 µm pore size.

More specifically, the utilized Chemicals and solvents were: Polyethylene oxide standard materials (abbreviated as PEOX 20 K and PEOX 30 K) were purchased from Agilent Technologies, Inc. Palo Alto, Calif., catalog number PL2083-1005 and PL2083-2005.

Acetonitrile (HPLC grade ≥99.9%, CHROMASOL plus), catalog number 34998, sodium hydroxide (semiconductor grade, 99.99%, trace metal base), catalog number 306576, water (HPLC grade, CHROMASOLV Plus) catalog number 34877 and sodium nitrate (99,995%, trace metal base) catalog number 229938 were purchased from Sigma-Aldrich, Switzerland.

Sodium dihydrogen phosphate (≥99.999% TraceSelect) catalog number 71492. was purchased from FLUKA, Switzerland.

The normalization solution of PEOX20 K at 5 mg/mL, the standard solution of PEOX30 K at 2 mg/mL, and the sample solution of HPMCAS at 2 mg/mL were prepared by adding a weighed amount of polymer into a vial and dissolving it with a measured volume of mobile phase. All solutions were allowed to dissolve at room temperature in the capped vial for 24 h with stirring using a PTFE-coated magnetic stirring bar.

The normalization solution (PEOX 20 k, single preparation, N) and the standard solution (PEOX30 K, double preparation, S1 and S2) were filtered into a HPLC vial through a syringe filter of 0.02 µm pore size and 25 mm diameter (Whatman Anatop 25, catalog number 6809-2002), Whatman.

The test sample solution (HPMCAS, prepared in duplicate, T1, T2) and a laboratory standard (HPMCAS, single preparation, LS) were filtered into a HPLC vial through a syringe filter of 0.45 µm pore size (Nylon, e.g. Acrodisc 13 mm VWR catalog number 514-4010).

Chromatographic condition and run sequence were conducted as described by Chen, R. et al.; Journal of Pharmaceutical and Biomedical Analysis 56 (2011) 743-748). The SEC-MALLS instrument set-up included a HP1100 HPLC system from Agilent Technologies, Inc. Palo Alto, Calif.; a DAWN Heleos II 18 angle laser light scattering detector and a OPTILAB rex refractive index detector, both from Wyatt Technologies, Inc. Santa Barbara, Calif. The analytical size exclusion column (TSK-GEL® GMPWXL, 300×7.8 mm) was purchased from Tosoh Bioscience. Both the OPTILAB and the DAWN were operated at 35° C. The analytical SEC column was operated at room temperature (24±5° C.). The mobile phase was a mixture of 40 volume parts of acetonitrile and 60 volume parts of aqueous buffer containing 50 mM NaH2PO4 and 0.1 M NaNO3 prepared as follows:

Aqueous buffer: 7.20 g of sodium dihydrogen phosphate and 10.2 g of sodium nitrate were added to 1.2 L purified water in a clean 2 L glass bottle under stirring until dissolution.

Mobile phase: 800 mL of acetonitrile were added to 1.2 L of the aqueous buffer prepared above, and stirred until a good mixture was achieved and the temperature equilibrated to ambient temperature. The mobile phase was pH adjusted to 8.0 with 10M NaOH and filtered through a 0.2 m nylon membrane filter. The flow rate was 0.5 mL/min with in-line degassing. The injection volume was 100 µL and the analysis time was 35 min The MALLS data were collected and processed by Wyatt ASTRA software (version 5.3.4.20) using dn/dc value (refractive index increment) of 0.120 mL/g for HPMCAS. The light scattering signals of detector Nos. 1-4, 17, and 18) were not used in the molecular weight calculation. A representative chromatographic run sequence is given below: B, N, LS, S1 (5×), S2, T1 (2×), T2 (2×), T3 (2×), T4 (2×), S2, T5(2×), etc., S2, LS, W, where, B represents blank injection of mobile phase, N1 represents normalization solution; LS represents a laboratory standard HPMCAS; S1 and S2 represent standard solutions one and two, respectively; T1, T2, T3, T4, and T5 represent test sample solutions and W represents water injection. (2×) and (5×) denote the number of injections of the same solution.

Both the OPTILAB and the DAWN were calibrated periodically according to the manufacturer's recommended procedures and frequency. A 100 µL injection of a 5 mg/mL polyethylene oxide standard (PEOX20 K) was employed for normalizing all angle light scattering detectors relative to 90° detector for each run sequence.

Use of this mono-dispersed polymer standard also enabled the volume delay between the OPTILAB and the DAWN to be determined, permitting proper alignment of the light scattering signals to the refractive index signal. This is necessary for the calculation of the weight-averaged molecular weight (Mw) for each data slice.

Production of HPMCAS According to Examples 1-2 and Comparative Examples A-B

Glacial acetic acid, acetic anhydride, a hydroxypropyl methylcellulose (HPMC), succinic anhydride and sodium acetate (water free) in the amounts listed in Table 1 below were utilized to produce HPMCAS. The HPMC had a methoxyl and hydroxypropoxyl substitution as listed in Table 2 below and a viscosity of about 3 mPa·s, measured as a 2% solution in water at 20° C. according to ASTM D2363-79 (Reapproved 2006). The HPMC is commercially available from. The Dow Chemical Company as Methocel E3 LV Premium cellulose ether.

In Examples 1 and 2, 230 g of HPMC (water free) was pre-dissolved at 85° C. in 170 g of acetic acid together with 50 g of sodium acetate (water free). Then 38.9 g of succinic anhydride and 170 g of acetic anhydride were added to the reactor under stirring. After 30 min of reaction time 150 g of sodium acetate (water free) was added to the reactor. In Example 1 the reaction mixture was allowed to react for further 120 min; in Example 2 the reaction mixture was allowed to react for further 180 min In Comparative Examples A and B, which are not prior art, glacial acetic acid, acetic anhydride, HPMC, succinic anhydride and sodium acetate (water free) were introduced in the amounts listed in Table 1 below into a reaction vessel under thorough stirring. Then the reaction mixture was heated at 85° C. with agitation. In Comparative Example A the reaction mixture was allowed to react for 120 min; in Comparative Example B the reaction mixture was allowed to react for 180 min After esterification, in each of the Examples 1 and 2 and the Comparative Examples A and B, 2.3 L of water was added to the reactor under stirring to precipitate the HPMCAS. The precipitated product was removed from the reactor and washed with 14-19 L of water by applying high shear mixing using an Ultra-Turrax stirrer S50-G45 running at 5200 rpm. The product was isolated by filtration and dried at 50° C. overnight.

Production of Comparative Example C

Glacial acetic acid, acetic anhydride, HPMC, succinic anhydride and sodium acetate (water free) were introduced in the amounts listed in Table 1 below into a reaction vessel under thorough stirring. The amounts of glacial acetic acid, acetic anhydride, HPMC, succinic anhydride and sodium acetate were those as disclosed in Comparative Example 3 of U.S. Pat. No. 5,776,501. The HPMC used in Comparative Example 3 of U.S. Pat. No. 5,776,501 had a viscosity of 8.9 mPa·s, measured as a 2% solution in water. However, to avoid that differences in HPMC viscosity have an impact on the molecular weight of the HPMCAS, the same HPMC was used in Comparative Example C as in Examples 1 and 2. The mixture was heated at 85° C. with agitation for 5 hours to effect esterification. 252.86 g of water was added to the reactor under stirring, followed by addition of 70.71 g concentrated hydrochloric acid (concentration of 37 wt-%). The precipitated product was obtained by adding the reaction mixture to 3.0 L of water under stirring (200 rpm). The crude product was washed with 11 L of water by applying high shear mixing using an Ultra-Turrax stirrer S50-G45 running at 5200 rpm. The product was isolated by filtration and dried at 55° C. for 12 h.

Comparative Example C was carried out a second time. The obtained ester substitutions % acetyl and % succinoyl in the repeated run of Comparative Example C were substantially the same as in the first run of Comparative Example C. The results in Table 2 show the average of the two runs of Comparative Example C.

Production of Comparative Examples D-H

Glacial acetic acid, acetic anhydride, HPMC, succinic anhydride and sodium acetate (water free) were introduced in the amounts listed in Table 1 below into a reaction vessel under thorough stirring. The weight ratios of glacial acetic acid, acetic anhydride, HPMC, succinic anhydride and sodium acetate were used as disclosed in Example 1 of U.S. Pat. No. 4,226,981, Table I, Sample Nos. 1-5. The U.S. Pat. No. 4,226,981 is silent about the viscosity of the used HPMC. To avoid that differences in HPMC viscosity have an impact on the molecular weight of the HPMCAS, the same HPMC was used in Comparative Example D-H as in Examples 1 and 2. The mixture was heated at 85° C. with agitation for 3 hours to effect esterification. 2.3 L of water was added to the reactor under stirring to precipitate the HPMCAS. The precipitated product was removed from the reactor and washed with 10 L of water by applying high shear mixing using an Ultra-Turrax stirrer S50-G45 running at 5200 rpm.

Production of Comparative Examples I and J

Glacial acetic acid, acetic anhydride, HPMC, succinic anhydride and sodium acetate (water free) were introduced in the amounts listed in Table 1 below into a reaction vessel under thorough stirring. The weight ratios of glacial acetic acid, acetic anhydride, HPMC, succinic anhydride and sodium acetate were used as disclosed International Patent Application WO 2005/115330, pages 51 and 52, polymers 1 and 3. The product was obtained, separated and washed as described in International Patent Application WO 2005/115330. The reaction mixture was quenched into 2.4 L of water, precipitating the polymer. An additional 1 L of water was used to complete the precipitation for example I only. The polymer was then isolated and washed with 3× 300 mL of water. Then the polymer was dissolved in 600 mL of acetone and again precipitated in 2.4 L of water. To complete precipitation another 1 L of water was added.

Production of HPMCAS of Comparative Examples K and L

Glacial acetic acid, acetic anhydride, HPMC, succinic anhydride and sodium acetate (water free) were introduced in the amounts listed in Table 1 below into a reaction vessel under thorough stirring. The weight ratios of glacial acetic acid, acetic anhydride, HPMC, succinic anhydride and sodium acetate were used as disclosed in Example 2 of European Patent Application EP 0219 426 A2.

The HPMC used in Comparative Examples K and L respectively had a viscosity of about 6 mPa·s and about 3 mPa·s respectively, measured as a 2% solution in water at 20° C. according to ASTM D2363-79 (Reapproved 2006). Each HPMC contained about 10% by weight of hydroxypropoxyl groups and about 29% by weight of methoxyl groups. These HPMC's are commercially available from The Dow Chemical Company as Methocel E6 LV Premium cellulose ether and Methocel E3 LV Premium cellulose ether respectively.

The mixture was heated at 85° C. with agitation for 3.5 hours to effect esterification. Water was added to the reactor under stirring to precipitate the HPMCAS. In Comparative Example K the amount of water was 1.2 L, and in Comparative Example L the amount of water was 2.4 L, respectively. The precipitated product was removed from the reactor and washed with an additional amount of water by applying high shear mixing using an Ultra-Turrax stirrer S50-G45 running at 5200 rpm. In Comparative Example K the additional amount of water was 12 L, and in Comparative Example L the additional amount of water was 11 L, respectively. The product was isolated by filtration and dried at 55° C. for 12 h. The product was then thoroughly washed and dried again as described in Examples 1-10.

Repetition of Comparative Examples K and L

Comparative Examples K and L were carried out a second time. The obtained ester substitutions % acetyl and % succinoyl in the repeated runs of Comparative Examples K and L were substantially the same as in the first runs of Comparative Examples K and L. The results in Table 2 show the average of the two runs for each of the Comparative Examples K and L.

Comparative Examples M, N-1, N-2, O-1 and O-2

HPMCAS samples were produced as described on pages 34 and 35 of WO 2011/159626. In Comparative Example M the recipe for HPMCAS-K(1) was exactly repeated. In Comparative Examples N-1 and N-2 the recipe for HPMCAS-K(2) and in Comparative Examples O-1 and O-2 the recipe for HPMCAS-K(3) were exactly repeated. Comparative Examples N and O were each conducted twice and reported as N-1, N-2, O-1 and O-2 respectively since the results in Comparative Examples N-1 and O-1 for $DOS_{Ac}$ and $DOS_S$ deviated from the results reported in WO 2011/159626 for HPMCAS-K(2) and HPMCAS-K(3).

Comparative Examples P to R

As disclosed in International Patent Application WO 2011/159626 on pages 1 and 2, HPMCAS is currently commercially available from Shin-Etsu Chemical Co., Ltd. (Tokyo, Japan), known by the trade name "AQOAT". Shin-Etsu manufactures three grades of AQOAT polymers that have different combinations of substituent levels to provide enteric protection at various pH levels, AS-L, AS-M, and AS-H, typically followed by the designation "F" for fine or "G", such as AS-LF or AS-LG. Their sales specifications are listed below.

Properties of AQOAT Polymers as Listed in WO 2011/159626

| Substituent content | Designation of analyzed commercial samples: Comparative Example | | |
|---|---|---|---|
| | P | Q | R |
| | Published Composition of AQOAT polymers (wt %) | | |
| | L-Grade | M-Grade | H-Grade |
| Methoxyl | 20.0-24.0 | 21-0-25.0 | 22.0-26.0 |
| Hydroxypropoxyl | 5.0-9.0 | 5.0-9.0 | 6.0-10.0 |
| Acetyl | 5.0-9.0 | 7.0-11.0 | 10.0-14.0 |
| Succinoyl | 14.0-18.0 | 10-14 | 4.0-8.0 |

Samples of the commercially available materials were analyzed as described further above.

The properties of the HPMCAS produced according to Examples 1-2 and comparative Examples A-O and the properties of the commercially available Comparative Examples P to R are listed in Table 2 below.

In Table 2 below the abbreviations have the following meanings:
$DS_M$=DS(methoxyl): degree of substitution with methoxyl groups;
$MS_{HP}$=MS(hydroxypropoxyl): molar subst. with hydroxypropoxyl groups;
$DOS_{Ac}$: degree of substitution of acetyl groups;
$DOS_S$: degree of substitution of succinoyl groups.

TABLE 1

| (Comparative) Example | HPMC* | | acetic acid mol/mol | | Succinic anhydride mol/mol | | Acetic anhydride mol/mol | | Sodium acetate mol/mol | | Heating at 85° C. hours |
|---|---|---|---|---|---|---|---|---|---|---|---|
| | g | Mol | g | HPMC | g | HPMC | g | HPMC | g | HPMC | |
| 1 | 230 g | 1.14 | 513 | 7.6 | 38.9 | 0.34 | 170 | 1.53 | 200 | 2.15 | 2 |
| A | 230 g | 1.14 | 513 | 7.6 | 38.9 | 0.34 | 170 | 1.53 | 200 | 2.15 | 2 |
| 2 | 230 g | 1.14 | 513 | 7.6 | 38.9 | 0.34 | 170 | 1.53 | 200 | 2.15 | 3 |
| B | 230 g | 1.14 | 513 | 7.6 | 38.9 | 0.34 | 170 | 1.53 | 200 | 2.15 | 3 |
| C | 150 | 0.74 | 450 | 10.1 | 35.8 | 0.48 | 57.43 | 0.79 | 59.57 | 0.98 | 5 |
| D | 115 | 0.57 | 575 | 16.9 | 138 | 2.44 | 57.5 | 1.03 | 115 | 2.47 | 3 |
| E | 115 | 0.57 | 575 | 16.9 | 92 | 1.63 | 57.5 | 1.03 | 115 | 2.47 | 3 |
| F | 115 | 0.57 | 575 | 16.9 | 57.5 | 1.02 | 115 | 2.06 | 115 | 2.47 | 3 |
| G | 115 | 0.57 | 575 | 16.9 | 46 | 0.81 | 138 | 2.48 | 115 | 2.47 | 3 |
| H | 115 | 0.57 | 575 | 16.9 | 34.5 | 0.61 | 184 | 3.30 | 115 | 2.47 | 3 |
| I | 80 | 0.40 | 420 | 17.7 | 18.9 | 0.48 | 640.2 | 16.53 | 40.43 | 1.25 | 21.75 |
| J | 80 | 0.40 | 420 | 17.7 | 13.2 | 0.33 | 432.8 | 11.17 | 40.43 | 1.25 | 21.75 |
| K[1)] | 100 | 0.49 | 300 | 10.1 | 25 | 0.51 | 38 | 0.78 | 80 | 1.97 | 3.5 |
| L[2)] | 200 | 0.96 | 600 | 10.2 | 50 | 0.51 | 76 | 0.78 | 160 | 1.97 | 3.5 |

*calculated on the dried basis
[1)] Comparative Example K: HPMC of 6 mPa · s
[2)] Comparative Example L: HPMC of 3 mPa · s

TABLE 2

| Table 2 (Comp.) Ex. | Molecular weight (kDA) | | | | | Recovery Rate (%) | 2% viscosity* (mPa · s) | Substitution | | Ester substitution | | Ether Substitution | | Ester substitution | |
|---|---|---|---|---|---|---|---|---|---|---|---|---|---|---|---|
| | $M_w$ | $M_n$ | $M_z$ | $M_w/M_n$ | $M_z/M_n$ | | | Methoxyl (%) | Hydroxy-Propoxyl, % | Acetyl (%) | Succinoyl (%) | $DS_M$ | $MS_{HP}$ | $DOS_{Ac}$ | $DOS_S$ |
| 1 | 126 | 57 | 585 | 2.2 | 10.3 | 102 | 2.74 | 23.6 | 7.5 | 8.4 | 11.3 | 1.92 | 0.25 | 0.49 | 0.28 |
| A | 96 | 32 | 800 | 3.0 | 25.0 | 99 | 2.76 | 23.7 | 7.4 | 8.6 | 11.2 | 1.93 | 0.25 | 0.51 | 0.28 |
| 2 | 139 | 63 | 589 | 2.2 | 9.1 | 103 | 2.65 | 23.5 | 7.4 | 8.9 | 11.6 | 1.93 | 0.25 | 0.53 | 0.29 |
| B | 131 | 40 | 1008 | 3.3 | 25.0 | 98 | 2.61 | 23.4 | 7.3 | 9.2 | 11.5 | 1.93 | 0.25 | 0.55 | 0.29 |

TABLE 2-continued

| Table 2 (Comp.) Ex. | Molecular weight (kDA) | | | | | Recovery Rate (%) | 2% viscosity* (mPa·s) | Ether Substitution | | Ester substitution | | Ether Substitution | | Ester substitution | |
|---|---|---|---|---|---|---|---|---|---|---|---|---|---|---|---|
| | $M_w$ | $M_n$ | $M_z$ | $M_w/M_n$ | $M_z/M_n$ | | | Methoxyl (%) | Hydroxy-Propoxyl, % | Acetyl (%) | Succinoyl (%) | $DS_M$ | $MS_{HP}$ | $DOS_{Ac}$ | $DOS_s$ |
| C | 53 | 23 | 342 | 2.3 | 14.9 | 103 | 2.90 | 23.7 | 7.6 | 5.8 | 14.7 | 1.96 | 0.26 | 0.35 | 0.37 |
| D | 37 | 25 | 56 | 1.5 | 2.2 | 102 | 3.06 | 20.1 | 6.4 | 2.6 | 25.0 | 1.79 | 0.24 | 0.17 | 0.68 |
| E | 38 | 25 | 65 | 1.5 | 2.6 | 104 | 2.89 | 21.6 | 6.6 | 3.3 | 22.7 | 1.90 | 0.24 | 0.21 | 0.61 |
| F | 41 | 23 | 111 | 1.8 | 4.8 | 98 | 2.92 | 21.6 | 7.0 | 6.2 | 15.8 | 1.79 | 0.24 | 0.37 | 0.40 |
| G | 40 | 22 | 123 | 1.8 | 5.6 | 101 | 2.98 | 23.1 | 7.2 | 7.8 | 13.5 | 1.92 | 0.25 | 0.47 | 0.34 |
| H | 36 | 20 | 119 | 1.8 | 6.0 | 101 | 3.73 | 23.5 | 7.6 | 9.7 | 9.6 | 1.90 | 0.25 | 0.57 | 0.24 |
| I | 51 | 23 | 462 | 2.2 | 20.1 | 105 | 2.86 | 22.3 | 7.4 | 11.7 | 11.7 | 1.90 | 0.26 | 0.72 | 0.31 |
| J | 54 | 22 | 1158 | 2.5 | 52.6 | 98 | 2.86 | 22.6 | 7.1 | 12.6 | 9.1 | 1.87 | 0.24 | 0.75 | 0.23 |
| K[1)] | 270 | 87 | 1060 | 3.1 | 12.2 | 101 | 4.58 | 21.9 | 7.2 | 5.6 | 16.8 | 1.83 | 0.25 | 0.34 | 0.43 |
| L[2)] | 65 | 26 | 329 | 2.5 | 12.7 | 95 | 2.89 | 22.9 | 7.3 | 5.7 | 16.0 | 1.91 | 0.25 | 0.34 | 0.41 |
| M | 427 | 94 | 2592 | 4.5 | 27.6 | 99 | 2.06 | 15.7 | 6.2 | 12.1 | 20.8 | 1.47 | 0.24 | 0.82 | 0.60 |
| N-1 | — | — | — | — | — | 71 | 2.05 | 16.2 | 6.3 | 14.3 | 16.6 | 1.47 | 0.24 | 0.94 | 0.46 |
| N-2 | — | — | — | — | — | 73 | 1.97 | 15.8 | 6.0 | 14.8 | 17.1 | 1.45 | 0.23 | 0.98 | 0.48 |
| O-1 | 234 | 39 | 2701 | 6.0 | 69.3 | 91 | 1.92 | 17.2 | 6.6 | 19.1 | 8.2 | 1.49 | 0.24 | 1.19 | 0.22 |
| O-2 | 143 | 25 | 2280 | 5.8 | 91.2 | 90 | 1.81 | 16.9 | 6.4 | 19.0 | 8.7 | 1.47 | 0.23 | 1.19 | 0.23 |
| P | 153 | 33 | 889 | 4.6 | 26.9 | 100 | 3.00 | 22.5 | 7.0 | 8.1 | 14.7 | 1.90 | 0.24 | 0.49 | 0.38 |
| Q | 104 | 25 | 512 | 4.2 | 20.5 | 100 | 3.00 | 23.2 | 7.2 | 9.4 | 10.8 | 1.89 | 0.24 | 0.55 | 0.27 |
| R | 137 | 29 | 821 | 4.7 | 28.3 | 97 | 3.00 | 23.6 | 7.2 | 11.5 | 7.8 | 1.90 | 0.24 | 0.67 | 0.19 |

*viscosity measured as a 2.0 wt % solution of the esterified cellulose ether in 0.43 wt % aqueous NaOH at 20° C.
[1)]Comparative Example K: HPMC of 6 mPa·s
[2)]Comparative Example L: HPMC of 3 mPa·s The results in Table 2 above illustrate that the esterified cellulose ethers of the present invention have a combination of a weight average molecular weight that makes them suitable as enteric polymers for pharmaceutical dosage forms and a high homogeneity, i.e. a low Polydispersity $M_w/M_n$ and a low $M_z/M_n$. Also, the measured weight average molecular weight $M_w$ of the produced HPMCAS was higher than could be expected based on the $M_w$ of the HPMC used as a starting material. The $M_w$ of the HPMC was about 20,000 Dalton. Taking the weight gain by the acetyl and succinoyl groups into account, an $M_w$ of about 25,000 Dalton (25 kDa) could be expected.

The comparisons between Example 1 and Comparative Example A and between Example 2 and Comparative Example B, respectively, illustrate the surprising fact that the inventive esterified cellulose ethers have a substantially lower ratio $M_z/M_n$ than comparable esterified cellulose ethers which have a produced from the same amounts of the same starting materials and which have the same amounts and types of ether and ester substituents and similar weight average molecular weights M.

The HPMCAS of Comparative Examples C-J and L have an unfavorably low $M_w$. Comparative Example K is not directly comparable with Examples 1-2 because the HPMCAS of Comparative Example K has been produced from a HPMC of higher viscosity. Even a 1.5 wt. % solution of the HPMCAS of Comparative Example K in acetone was gel-like. Such HPMCAS would not be useful in end-uses such as spray-drying which typically start from solutions comprising at least 7 weight percent, more typically at least 10 weight percent of the esterified cellulose ether.

The HPMCAS of Examples 1 and 2 have an Mw in the same range as the Mw of Comparative Examples O-2 and P-R, but a lower polydispersity $M_w/M_n$ and a much lower $M_z/M_n$ than Comparative Examples O-2 and P-R. The combination of high weight average molecular weight $M_w$, reasonably low $M_w/M_n$ and low $M_w/M_n$ makes the esterified cellulose ether of the present invention very suitable as enteric polymer for pharmaceutical dosage forms. Moreover, the low turbidity and low viscosity in acetone facilitates the processing of the HPMCAS and their incorporation into pharmaceutical dosage forms, such as in spray-drying processes.

The HPMCAS of Examples 1 and 2 also have a significantly lower polydispersity $M_w/M_n$ and a much lower $M_z/M_n$ than Comparative Examples M and O-1.

In the HPLC method utilized for determination of $M_w$, $M_n$ and $M_z$, in Examples 1-2 and in Comparative Examples A to M and O-R a very good recovery rate (=[weight of HPMCAS recovered from HPLC column/weight of HPMCAS introduced into HPLC column]×100) was achieved, which allowed a reliable determination of $M_w$, $M_n$ and $M_z$. However, in Comparative Examples N-1 and N-2 the recovery rate was too low to make a reasonably reliable $M_w$, $M_n$ and $M_z$ determination.

TABLE 3

| (Comp.) Example | Turbidity 1.5 wt. % in acetone, [NTU] | 10% viscosity in acetone [mPa·s] | $M_w$ | $M_n$ | $M_z$ | $M_w/M_n$ | $M_z/M_n$ |
|---|---|---|---|---|---|---|---|
| 1 | 14.6 | 17.4 | 126 | 57 | 585 | 2.2 | 10.3 |
| A | 19.8 | 18.7 | 96 | 32 | 800 | 3.0 | 25.0 |
| 2 | 15.9 | 18.3 | 139 | 63 | 589 | 2.2 | 9.3 |
| B | 22.4 | 21.7 | 131 | 40 | 1008 | 3.3 | 25.2 |
| L | 13.1 | 16.6 | 65 | 26 | 329 | 2.5 | 12.7 |
| P | 39.4 | 27.7 | 153 | 33 | 889 | 4.6 | 26.9 |
| Q | 43.7 | 22.9 | 104 | 25 | 512 | 4.2 | 20.5 |
| R | 42.4 | 29.8 | 137 | 29 | 821 | 4.7 | 28.3 |

The results in Table 3 illustrate that the esterified cellulose ethers of the present invention have a higher homogeneity as well as a lower turbidity and a lower viscosity in acetone than esterified cellulose ethers of comparable weight average molecular weight $M_w$ that are either known (Comparative Examples P-R) or that have been prepared according to a generally known procedure (Comparative Examples A and B). Moreover, the HPMCAS of Examples 1 and 2 exhibit a turbidity and viscosity in acetone which are not much higher than that of Comparative Example L although the $M_w$ of the HPMCAS of Examples 1 and 2 is about twice as high as the $M_w$ of the HPMCAS of Comparative Example L.

The invention claimed is:

1. An esterified cellulose ether having
    i) as ester groups aliphatic monovalent acyl groups or a combination of aliphatic monovalent acyl groups and groups of the formula
    —C(O)—R—COOA wherein R is a divalent aliphatic or aromatic hydrocarbon group and A is hydrogen or a cation,
    ii) a weight average molecular weight Mw of from 80,000 Dalton to 220,000 Dalton,
    iii) a Polydispersity Mw/Mn of from 1.3 to 4.0, and
    iv) an Mz/Mn of not more than 18.5,
    when the weight average molecular weight Mw, the number average molecular weight Mn and the z-average molecular weight Mz are measured by SEC-MALLS using as mobile phase a mixture produced from 40 parts by volume of acetonitrile and 60 parts by volume of aqueous buffer containing 50 mM $NaH_2PO_4$ and 0.1 M $NaNO_3$.

2. The esterified cellulose ether of claim 1 wherein the aliphatic monovalent acyl groups are acetyl, propionyl or butyryl groups and the groups of the formula —C(O)—R—COOA are —C(O)—CH2-CH2-COOA,
    —C(O)—CH═CH—COOA, or —C(O)—C6H4-COOA.

3. The esterified cellulose ether of claim 1 being hydroxypropyl methyl cellulose acetate succinate.

4. The esterified cellulose ether of claim 1 having a weight average molecular weight Mw of from 90,000 to 185,000 Dalton.

5. The esterified cellulose ether of claim 1 having an Mw/Mn of from 1.5 to 3.5 or an Mz/Mn of from 3.0 to 17.0, or a combination thereof.

6. A composition comprising a liquid diluent and at least one esterified cellulose ether of claim 1.

7. The composition of claim 6 additionally comprising at least one active ingredient and optionally one or more adjuvants.

8. A solid dispersion comprising at least one active ingredient in at least one esterified cellulose ether of claim 1.

9. The solid dispersion of claim 8 in the form of strands, pellets, granules, pills, tablets, caplets, microparticles, fillings of capsules or injection molded capsules or in the form of a powder, film, paste, cream, suspension or slurry.

10. A process for producing the solid dispersion of claim 8 comprising the steps of blending a) at least one esterified cellulose ether of claim 1, b) one or more active ingredients and c) one or more optional additives, and subjecting the blend to extrusion.

11. A process for producing the solid dispersion of claim 8 comprising the steps of blending
    a) at least one esterified cellulose ether having i) as ester groups aliphatic monovalent acyl groups or a combination of aliphatic monovalent acyl groups and groups of the formula —C(O)—R—COOA, wherein R is a divalent aliphatic or aromatic hydrocarbon group and A is hydrogen or a cation, ii) a weight average molecular weight Mw of from 80,000 Dalton to 220,000 Dalton, iii) a Polydispersity Mw/Mn of from 1.3 to 4.0, and iv) an Mz/Mn of not more than 18.5, when the weight average molecular weight Mw, the number average molecular weight Mn and the z-average molecular weight Mz are measured by SEC-MALLS using as mobile phase a mixture produced from 40 parts by volume of acetonitrile and 60 parts by volume of aqueous buffer containing 50 mM $NaH_2PO_4$ and 0.1 M $NaNO_3$,
    b) one or more active ingredients,
    c) one or more optional additives, and
    d) a liquid diluent to prepare a liquid composition, and removing said liquid diluent.

12. A dosage form being coated with the esterified cellulose ether of claim 1.

13. A capsule shell comprising the esterified cellulose ether of claim 1.

14. A process for producing an esterified cellulose ether of claim 1 comprising the steps of
    (A) dissolving or dispersing a cellulose ether and a first amount of alkali metal carboxylate in a reaction diluent,
    (B) heating the obtained mixture to a temperature of 60° C. to 110° C. before, during or after adding (i) an aliphatic monocarboxylic acid anhydride or (ii) a combination of an aliphatic monocarboxylic acid anhydride and a dicarboxylic acid anhydride to the mixture obtained in step (A), and allowing the esterification reaction to proceed, and
    (C) before the esterification reaction in step (B) is completed, adding a second amount of alkali metal carboxylate and allowing the esterification reaction to further proceed,
    wherein the esterified cellulose ether product has
    i) as ester groups aliphatic monovalent acyl groups or a combination of aliphatic monovalent acyl groups and groups of the formula —C(O)—R—COOA wherein R is a divalent aliphatic or aromatic hydrocarbon group and A is hydrogen or a cation,
    ii) a weight average molecular weight Mw of from 80,000 Dalton to 220,000 Dalton,
    iii) a Polydispersity Mw/Mn of from 1.3 to 4.0, and
    iv) an Mz/Mn of not more than 18.5,
    when the weight average molecular weight Mw, the number average molecular weight Mn and the z-average molecular weight Mz are measured by SEC-MALLS using as mobile phase a mixture produced from 40 parts by volume of acetonitrile and 60 parts by volume of aqueous buffer containing 50 mM $NaH_2PO_4$ and 0.1 M $NaNO_3$.

15. The process of claim 14 wherein the first amount of alkali metal carboxylate added in step (A) is 15 to 35 percent and the second amount of alkali metal carboxylate added in step (B) is 65 to 85 percent, based on the total amount of added alkali metal carboxylate in the process.

16. The esterified cellulose ether of claim 3 having a weight average molecular weight Mw of from 90,000 to 185,000 Dalton.

17. The esterified cellulose ether of claim 16 having an Mw/Mn of from 1.5 to 3.5 or an Mz/Mn of from 3.0 to 17.0, or a combination thereof.

* * * * *